United States Patent [19]

Van de Velde

[11] Patent Number: 5,646,416

[45] Date of Patent: Jul. 8, 1997

[54] RADIATION IMAGE IDENTIFYING DEVICE

[76] Inventor: Stefan Van de Velde, c/o Agfa-Gevaert N.V., DIE 3800, Septestraat 27, B, 2640 Mortsel, Belgium

[21] Appl. No.: 403,622

[22] Filed: Mar. 14, 1995

[30] Foreign Application Priority Data

Mar. 22, 1994 [EP] European Pat. Off. ............ 94200733.7

[51] Int. Cl.$^6$ .................................................. G01N 23/04
[52] U.S. Cl. ............................................................ 250/584
[58] Field of Search ...................................... 250/584, 583; 364/413, 13

[56] References Cited

U.S. PATENT DOCUMENTS 5,229,618  7/1993  Fuji .
5,241,472  8/1993  Gur et al. ............................ 364/413.22
5,321,520  6/1994  Inga et al. .............................. 358/403
5,400,792  3/1995  Hoebel et al. ........................ 128/670

FOREIGN PATENT DOCUMENTS 0077999  4/1983  European Pat. Off. .
9214403  9/1992  WIPO .

*Primary Examiner*—David P. Porta
*Assistant Examiner*—David Vernon Bruce
*Attorney, Agent, or Firm*—Richard J. Birch

[57] ABSTRACT

A universal radiation image identification system for use in an environment such as a hospital wherein an information management system is already available. The identification system is interfaced to the existing information system in order to avoid reentering the identification data with respect to radiological data. The radiological data or image typically is stored in a photostimulable phosphor screen.

6 Claims, 5 Drawing Sheets

```
0010.0010.SMITH(CR)
0010.1001.HELEN(CR)
0010.0020.123KLM(CR)
0010.0040.F(CR)
0010.0030.19550525(CR)
0019.4000.CHEST(CR)
0019.4001.GENERAL(CR)
0019.1262.100(CR)
0008.1060.PROF ENGLISH(CR)
0020.0020.PA(CR)
0021.0040.VERTICAL(CR)
0020.4000.(CR)
0000.5170.1(CR)
(EOF)
```

IDENTIFICATION

| | |
|---|---|
| PATIENT NAME: | SMITH |
| FIRST NAME: | HELEN |
| PATIENT CODE: | 123KLM |
| SEX: | F |
| DATE OF BIRTH: | 25:05:1955 |
| | |
| RADIOLOGIST: | PROF. ENGLISH |
| EXAM: | CHEST            GENERAL |
| PATIENT POSITION: | PA |
| CASSETTE POSITION | VERTICAL |
| EXPOSURE CLASS: | 100 |
| COMMENT: | |
| | |
| COPIES: | 1 |

PRESS ENTER TO CONFIRM OR SPACE BAR FOR SELECTION MENU

FIG. 5

RADIATION IMAGE IDENTIFYING DEVICE

DESCRIPTION

1. Field of the Invention

The present invention is in the field of digital radiography and relates to the identification of a radiation image. More in particular it relates to identification of a radiation image in a system for reading and processing a radiation image that has been stored in a photostimulable phosphor screen, said system being installed in an environment such as a hospital wherein an information management system is already available.

2. Description of the Prior Art

In the field of digital radiography a wide variety of image acquisition techniques have been developed that render a digital representation of a radiation image.

In one of these techniques a radiation image, for example an x-ray image of an object, is stored in a screen comprising a photostimulable phosphor such as one of the phosphors described in European patent publication 503 702 published on 16.09.92.

In a read out station the stored radiation image is read by scanning the screen with stimulating radiation such as laser light of the appropriate wavelength, detecting the light emitted upon stimulation and converting the emitted light into an electric representation for example by means of an adequately adjusted photomultiplier and finally digitizing the signal.

After readout the residual image left on the photostimulable phosphor screen is erased so that the screen is again available for exposure.

The digital image signal is then processed on-line. It is further possible to sent the image signal to an off-line workstation where the image signal can be subjected to additional processing steps.

It can also be transmitted to a laser recorder for reproduction of the processed image on the film size and lay-out of the radiologist's choice and/or it can be applied to a monitor for display.

Prior to read out, the radiation image is identified, i.e. at least patient identification data and examination data are associated with the radiation image.

In one example of a system of the above described kind the photostimulable phosphor screen is conveyed in a cassette and the identification data are associated with the cassette prior to exposure. More specifically a memory chip is embedded in the cassette and patient demographic data as well as examination data are written into this memory device. Since the memory chip is embedded in the cassette, the data are automatically linked to the image and remain linked during read-out and processing.

In a stand alone read out system the identification procedure operates as follows. The cassette conveying a photostimulable phosphor screen is first introduced into the identification station for identification. Via the keyboard and a user-friendly menu patient demographics are entered and examination data are selected.

The patient data and the examination data or at least an indication thereof are written into the memory chip that is mounted on the cassette.

Then the screen is exposed. Alternatively the screen can be exposed prior to identification.

After identification and exposure the cassette is taken to the read out station where the information stored in the memory chip is read out. This information is used when adjusting the read out means and when selecting parameters for the processing of the image. Then, the latent image stored in the photostimulable phosphor screen is effectively read out, digitized and processed.

However, a system as described hereinbefore is often installed in a hospital environment where one already disposes of an information management system.

Large hospitals often have a 'Hospital Information System (HIS)' or a 'Radiology Information System (RIS)' which is a repository of validated patient, clinical and administrative information and which connects to data or image handling equipment.

Others use a card read system or a bar code reader for identifying patients in several departments of the hospital such as the administrative department, the radiology department etc.

When a radiation image read out system and the associated identification station, is added to the equipment already installed in a hospital, the patient and examination identification process which has in most cases already been performed in some part of the hospital, for example at the administration desc, is to be repeated at the identification station of the read out system.

This is a time-consuming operation for both the operator and the patient. The repeated identification of patient and examination type decreases the operational speed of the entire system and may be the cause of mistakes and inconsistencies.

Dedicated systems have been developed to interface existing information systems with an identification system such as an identification station part of a system for computed radiography using photostimulable phosphor screens.

The following article describes one example of an identification system for radiation images that makes use of an already existing information management system: "Data interface between a radiology information system and a computed radiography system using personal computer and standard software" published by Joaquim Piqueras and Joan-Carles Carreno in AJR 1993; 161:1313–1315.

This article describes that identification data for the computed radiography system are obtained directly from the radiology information system. The system uses DESQview-386 V.2.2 software (Quarterdeck Office Systems) which is an MS-DOS program that runs several MS-DOS (Microsoft Corp.) or Windows (Microsoft Corp.) programs in different screen windows simultaneously.

It allows side-by-side operation of the RIS (Radiology Information System) software and the application run on a computed radiography terminal. The described system opens two windows: one running on the software of the computed radiography system and the other running on the software of the information system. Data appearing in one window can be cut and pasted to the other window.

This article addresses the same problem as our invention, the proposed solution however is not universal, it is only applicable in a DOS/WINDOWS environment.

Since a wide variety of information systems exists at the moment and the number of data structure standards and methodologies is immense and a common protocol is not installed on each of the available systems, it is normally not possible to transfer measures taken to establish interfacing of one set of devices to another set.

Objects of the Invention

It is an object of the present invention to provide a system for identifying a radiation image that makes use of the existing modalities in a hospital and that avoids reentering of identification data.

It is a further object of the present invention to provide interfacing of an identification station with a wide variety of existing information systems such as a data base management system or a magnetic card system or a bar-code reader etc.

It is an object to provide such a system in connection with a system for reading a radiation image that has been stored in a photostimulable phosphor screen.

Further objects will become apparent from description hereinafter.

Statement of the Invention

To achieve the above objectives the present invention provides a radiation image identification system comprising an information system supplying patient identification data, an identification station for running a procedure identifying a radiation image of a patient, a network system interfacing said identification station and said information system, data interchange means enabling interchange of data between said information system and said identification station interconnected by said network system, conversion means for converting a format wherein identification data are supplied by said information system into a format that is interpretable by said identification station, characterised in that said identification station comprises means for interrupting said identification procedure and for initiating operation of said data interchange means and said conversion means, means for storing data converted by said conversion means, and means for resuming said identification procedure upon termination of said conversion by means of said converted data.

The present invention is advantageous in that the operator of the identification station gets access to data stored in an information system such as a hospital information system.

The workload of the operator of the identification station decreases as patient data need not to be re-typed. Typing errors are made impossible. In this way the identification speed as well as the accuracy is increased.

The interfacing of an identification station with an information system is generally performed by means of the following two elements: a physical connection between the identification station and the information system (Radiology Information System or Hospital Information System) and a protocol implemented by either of these systems so as to provide control and interchange of data such as demographic patient data and examination data.

The physical connection can be realized by implementing a local area network (LAN) or by means of a serial or parallel point-to-point connection. A wide variety of suitable physical connections are available on the market: Ethernet (trademark of Xerox corporation), FDDI (Fiber distributed data interchange), Netware (trademark of Novell Inc.), RS232, SCSI, etc.

To enable data interchange between two systems a protocol is required, said protocol defining a number of commands that are identically interpreted by either of the systems. A protocol can be implemented up to different levels of the OSI seven layer model. Suitable protocols that make data of linked systems accessible in the form of a file or as byte-streams are commercially available for numerous hardware platforms. Examples are: NFS (trademark of Sun Microsystems), TCP-IP, TLI sockets etc.

For medical applications dedicated protocols such as ACR-NEMA, DICOM ... or extended protocols such as SPI ... have been developed. Implementations of these protocols are not yet available for all platforms.

Therefore our invention provides means for converting data formats so that the data format applied in the information system can be converted into a data format that is interpretable by the identification station.

In accordance with our invention means are provided that interrupt the identification procedure running on an identification station so as to start operation of conversion means that convert data from the format in which they are available in the information system into the format that is readable by the identification station.

Next, upon termination of the operation of the data conversion means, the identification station resumes its identification procedure by means of the converted data.

Our invention is particularly suitable in an environment such as a hospital or a radiology department in which an identification system is added to the equipment already installed in said environment, said equipment comprising an information management system.

It is preferred in such an environment that the means for converting data are provided by the customer being the technicians who are acquainted with the available information system so that data conversion can be obtained without requiring that the company that installs the identification station has complete knowledge of the existing equipment.

This way of operating is advantageous in that the identification station does not bother about the format in which data are generated at the side of the information system and the identification station does not need to be designed so as to be able to interpret data available on the existing information system.

In this way a 'universal' identification station can be designed that can use data from any kind of information system without the need of developing a dedicated protocol or dedicated interface routines.

In a specific embodiment the identification station is used to identify a radiation image that is stored on a photostimulable phosphor screen. The identification system as described higher is then used together with a system for reading a radiation image that has been stored in a photostimulable phosphor screen comprising means for scanning said screen with stimulating irradiation, means for detecting the light emitted upon stimulation and means for converting the detected light into an electric signal representation.

The identification data that are entered at the identification station are written into a memory device, more specifically a electrically erasable read only memory that has been embedded into the cassette conveying the photostimulable phosphor screen.

The cassette is introduced in a read out device where it is opened; wherein the information stored in the EEPROM is read and where the screen is scanned with stimulating irradiation, the light emitted upon stimulation is detected and converted into an electric signal representation.

The identification procedure works as follows in case link exists between an identification station and an existing information system (Radiology information system RIS or Hospital information system HIS):

When a patient enters the hospital, the operator of the existing information system enters the demographic data and the patient is ready for exposure.

The patient then goes to the radiology department where the operator of the identification station then starts an identification procedure that in its turn calls a routine supplied by the customer to retrieve and convert the prepared data to a specific file format. The software of the identification station uses this file to fill in the identification screen.

The operator can edit or accept the displayed information and finally write the identification information into the memory on the cassette.

The identification station can also be linked to alternative systems such as a magnetic card system or a bar code reading system. The identification procedure then works in a similar way. The identification station is not capable of reading all magnetic card formats. Therefore a customer program has to be developed to read the data from the magnetic card and put the data in a file on the hard disc of the identification station.

The identification software in the identification station calls the customer program, this customer program prepares the data-i.e. reads the magnetic card- and prepares a data file. The customer program then stops and returns to the identification program.

This program reads the data from the file and enters the relevant fields in the identification screen.

In case of a bar code reader, the bar code is translated into a number by the bar code scanner, the customer program uses this key to consult a remote database and gets relevant patient information. The customer program stores this data in the data file and comes to a halt. Then the identification station reads the data from the file and enters relevant fields in the identification screen.

Still other alternatives are possible.

BRIEF DESCRIPTION OF THE DRAWINGS

Particular aspects of the present invention as well as preferred embodiments thereof will be explained by means of the corresponding drawings wherein

FIG. 5 illustrates the conversion of data retrieved from a HIS into a format that is readable by the identification station.

A radiation image of an object was recorded on a photostimulable phosphor screen 3 by exposing (radiation emitted by source 2) said screen to x-rays transmitted through the object (not shown). The stimulable phosphor screen 3 was conveyed in a cassette provided with an electrically erasable programmable read only memory (EEPROM) and a galvanic data transmission. A cassette of this kind has been described in U.S. Pat. No. 4,960,994.

The radiation image was first identified in an identification station 4 consisting of a standard PC-based computer with keyboard, monitor and a cassette insertion port.

In this identification station all kinds of data such as patient examination data can be entered via the keyboard. Alternatively these data can be retrieved from another information system such as a Radiology Information System (RIS).

Figure 2:
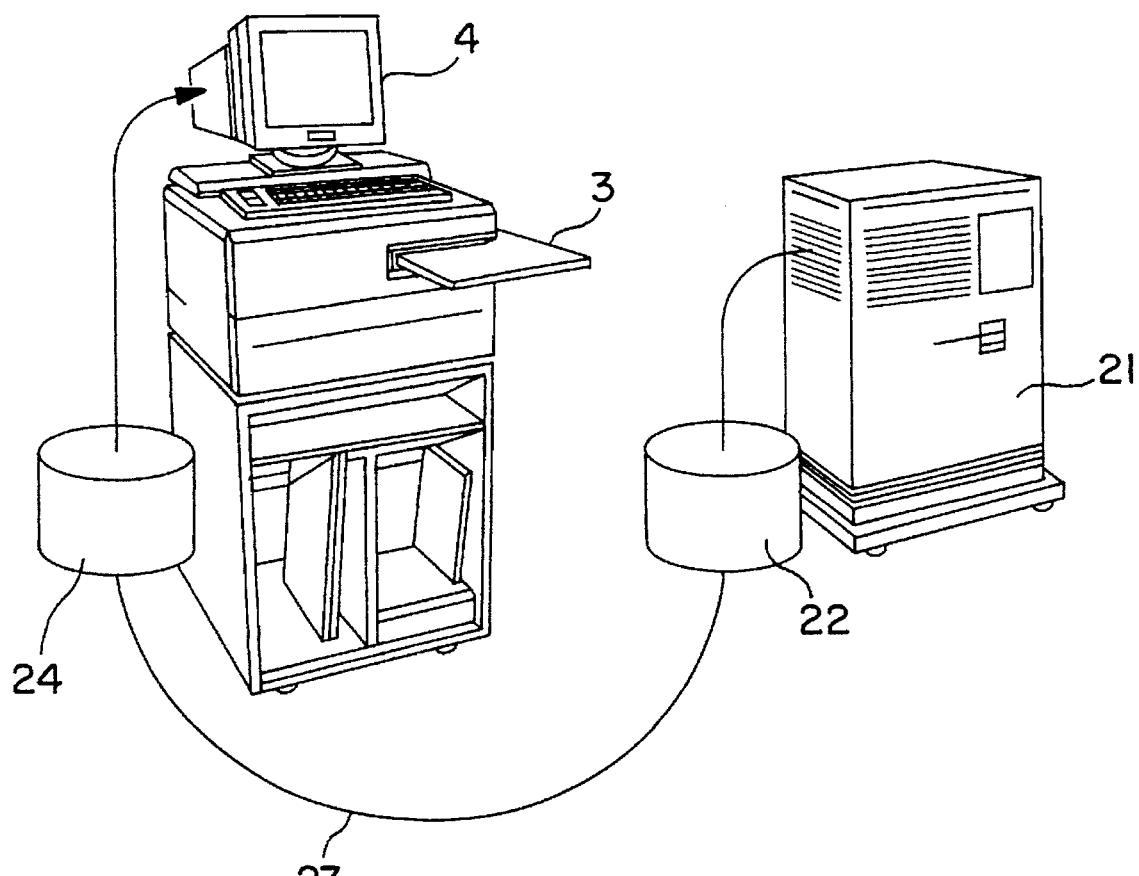
FIG. 2 shows the interfacing of an identification station and a hospital information system.

In the described embodiment patient identification data were retrieved from a radiology information system as is shown in FIG. 2.

The radiologic information system was a private hospital software running on Apple Macintosh. This system handles patient identification, registration, scheduling, reporting etc.

The identification station and the hospital information system communicated via an Ethernet link (23) running TCP-IP and PC NFS.

The patient and examination data were available on the radiology information system (21) in a relational database (RDBMS). All data were stored on a local disc (22).

Figure 3:
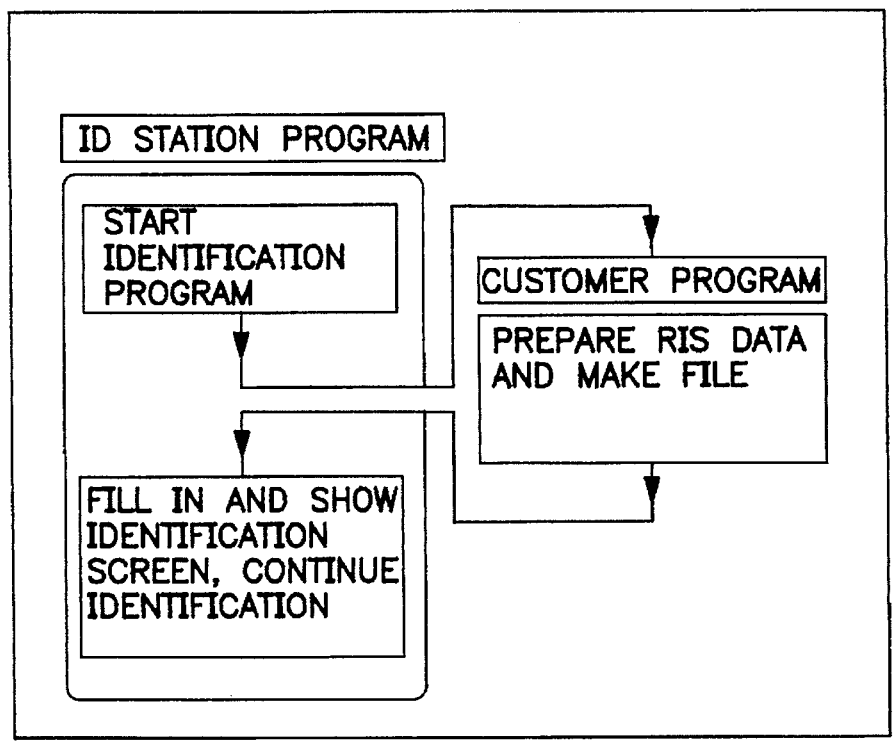
FIG. 3 and 4 are block schemes illustrating the identification system according to the present invention.
Figure 4:
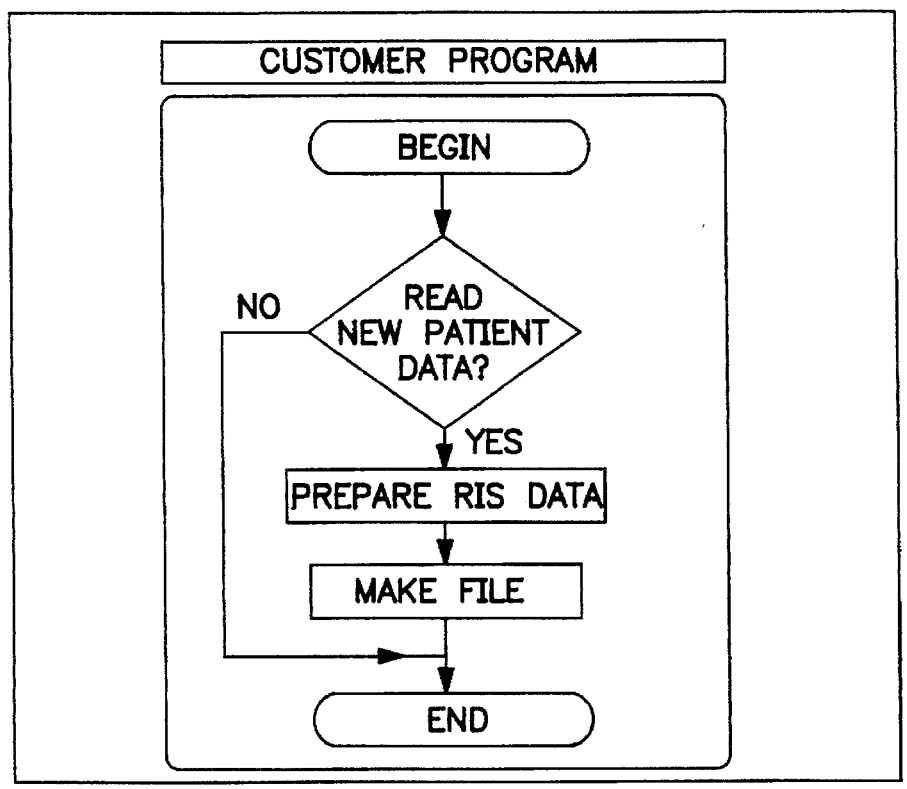

FIG. 3 illustrates the operation of the identification procedure. During the identification procedure, the identification program running on the PC-based identification station (4) is interrupted and by means of a software implemented routine an external customer program is called that creates or retrieves the data from the radiology information system and places these data in a file. FIG. 4 illustrates this customer program.

More in particular: upon insertion of a cassette containing a photostimulable phosphor screen (3), a customer program was called that provided display of a screen enabling selection by the operator of a patient name out of a list of scheduled patients.

Then, an examination type was selected from a list of examinations scheduled for this patient.

The custom program ended with the creation of an ASCII file on disc (22) of the RIS system.

A disc partition of disc (22) was logically attached to the identification station disc (24) by means of the PC-NFS package which made the created file available on the identification station.

The identification program running on the identification station continued by a command providing reading the file and filling the screen with the available data.

Hereafter it was still possible to modify the displayed values. Then, the data were stored on the cassette.

The created file was in a standard structure ready for use by the identification station. All characters contained in the file had to be interpreted as ASCII characters. The data format consisted of three fields for every data element. Every field was separated by a comma, and every element ended with the ASCII character 13 (CR).

The first two field described the data element derived from the ACR-NEMA standard (ACR-NEMA stands for American College of Radiologist-National Electronical Manufacturers Association) which is a standard for electronic data interchange.

The ACR-NEMA standard defines two codes that are expressed as ASCII hexadecimal numbers:
ACR-NEMA group number and ACR-NEMA element number. The third field contains the actual data in a standard ASCII string.

FIG. 5 gives an overview of supported fields with a description of the data field.

If a data field is not available, it can be omitted. In this case, the identification station will replace these fields with a default as possible.

When the data file has been created, the customer program exits and the identification software on the identification station continues its operation.

Selection of an examination type was performed by making a selection among menu items that were displayed upon entering a radiologist's name. With the selected examination process a number of parameters and keys regarding adjustments of the read out apparatus, image processing and image layout were associated.

Once patient identification data were retrieved from the hospital information system and a selection among examination types was performed, the relevant data were written onto the memory device provided on the cassette conveying the photostimulable phosphor screen.

Figure 6:
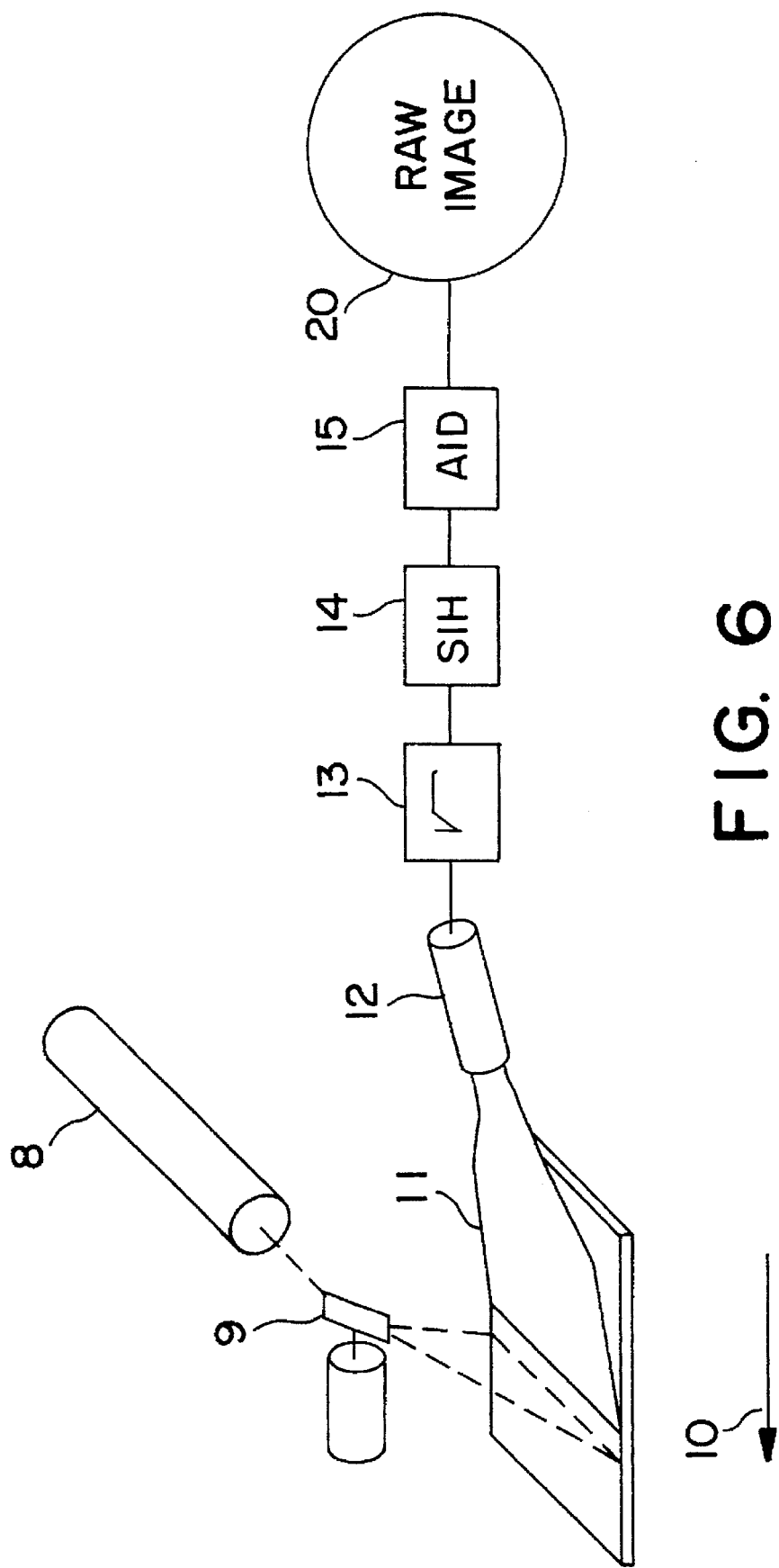
FIG. 6 is a more detailed view of a system for reading an image stored in a photostimulable phosphor screen.

Next the cassette was fed into a radiation image read-out apparatus 1 where the information stored in the EEPROM and the image stored in the photostimulable phosphor screen were read-out. Image read out is illustrated in FIG. 6. The stored image was read-out by scanning the phosphor screen with stimulating rays emitted by a laser 8. The stimulating rays were deflected into the main scanning direction by means of galvanometric deflection 9. The sub-scanning was performed by transporting the phosphor screen in the sub-scanning direction indicated by arrow 10. The stimulated emission was directed by means of a light collector 11 onto a photomultiplier 12, for conversion into an electrical image representation. Next, the signal was amplified by a square root amplifier 13, sampled by a sample and hold circuit 14, and converted into a 12 bit signal by means of an analog to digital convertor 15.

The digital raw image signal 20 was then sent to the image processing module of the read-out apparatus (FIG. 1, numeral 7) where it was stored in an internal buffer. The digital image signal was subjected to a decomposition into detail images at multiple resolution levels and a residual image.

The multi-resolution representation of the image was then subjected to an image quality enhancing modification and the modified multi-resolution representation was finally subjected to a reconstruction process.

Figure 1:
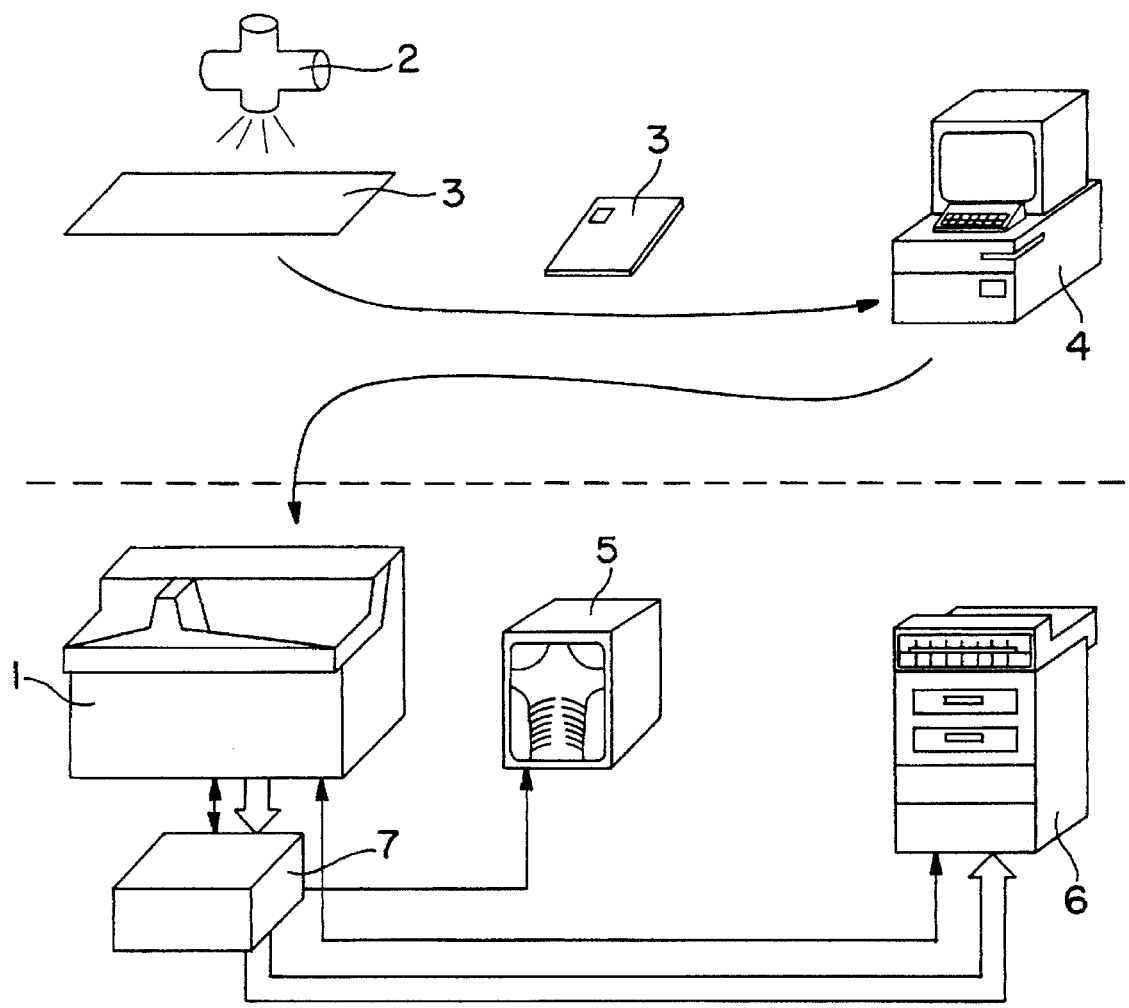
FIG. 1 is a computed radiography system.

The image was also sent to a preview monitor, indicated by numeral 5 in FIG. 1, which gave a first impression of the acquired image and hence provided early feedback to the operator in case the acquisition went wrong.

The decomposed digital image signal was also sent to a workstation (not shown). The workstation allows performing a variety of operations such as viewing the digitized image on screen, collimation, zoom etc.

The system was also connected to a laser imager (6) to print the images on high quality laser film.

I claim:

1. A radiation image identification system comprising an information system comprising a data base having stored therein identification data of a number of patients, an identification station arranged to identify a radiation image of a patient on the basis of patient identification data retrieved from said information system, a network system interfacing said identification station and said information system, data interchange means enabling interchange of data between said information system and said identification station connected by said network system, means for converting the format of data supplied by said information system into a format that is interpretable by said identification station, wherein said identification station comprises means for initiating operation of said data interchange means and said conversion means, means for storing converted data, and means for resuming identification upon termination of said conversion by means of said converted data.

2. A system for reading a radiation image that has been stored in a photostimulable phosphor screen comprising an image read out section comprising means for scanning said screen with stimulating irradiation, means for detecting light emitted upon stimulation, means for converting said light into a digital signal representation, an information system comprising a data base having stored therein identification data of a number of patients, an identification station arranged to identify a radiation image of a patient on the basis of patient identification data retrieved from said information system, a network system interfacing said identification station and said information system, data interchange means enabling interchange of data between said information system and said identification station connected by said network system, means for converting the format of data supplied by said information system into a format that is interpretable by said identification station, wherein said identification station comprises means for initiating operation of said data interchange means and said conversion means, means for storing converted data, and means for resuming said identification upon termination of said conversion by means of said converted data.

3. A system according to claim 2 wherein said screen is conveyed in a cassette that is provided with a memory device and wherein said identification station is provided with means for writing identification data into said memory device.

4. A system according to claim 3 wherein said memory device is an electrically erasable programmable memory (EEPROM).

5. A method of identifying a radiation image by means of an identification procedure running on an identification station that is connected to an information system supplying data to said identification station via a network, characterised in that (1) said identification procedure is interrupted, (2) data supplied by said information system are converted so that the data format wherein data are supplied by said information system is converted into a format that is interpretable by said identification station, (3) converted data are stored, (4) identification is resumed by means of said converted data.

6. A method according to claim 5 wherein said radiation image is stored in a photostimulable phosphor screen.

* * * * *